United States Patent [19]

Pahlmark et al.

[11] Patent Number: 5,540,885
[45] Date of Patent: Jul. 30, 1996

[54] STERILIZATION PROCESS

[75] Inventors: Kristian Pahlmark, Höganas; Git Persson, Helsingborg, both of Sweden

[73] Assignee: W.R. Grace & Co. - Conn., New York, N.Y.

[21] Appl. No.: 199,273

[22] PCT Filed: Jun. 30, 1993

[86] PCT No.: PCT/SE93/00604

§ 371 Date: Aug. 22, 1994

§ 102(e) Date: Aug. 22, 1994

[87] PCT Pub. No.: WO94/01143

PCT Pub. Date: Jan. 20, 1994

[30] Foreign Application Priority Data

Jan. 7, 1992 [SE] Sweden .................. 9202035

[51] Int. Cl.$^6$ ....................................... A61L 2/00
[52] U.S. Cl. .................. 422/28; 53/426; 422/1; 422/32; 422/37; 422/40; 426/399
[58] Field of Search .................... 422/1, 28, 32, 422/34, 37, 40; 426/399 X, 407, 409; 53/11 R, 111 RC, 425, 426; 427/331, 444

[56] References Cited

U.S. PATENT DOCUMENTS

| | | | |
|---|---|---|---|
| 3,163,971 | 1/1965 | Löliger et al. | 426/399 X |
| 3,924,013 | 12/1975 | Kane | 426/407 X |
| 4,152,464 | 5/1979 | Brody et al. | 426/399 X |
| 4,533,515 | 8/1985 | Witter et al. | 426/407 |
| 4,615,924 | 10/1986 | Hekal et al. | 426/407 X |
| 5,008,076 | 4/1991 | Johansson et al. | 422/28 |
| 5,225,055 | 7/1993 | Sibley et al. | 204/131 |
| 5,302,345 | 4/1994 | Oksman et al. | 422/30 |
| 5,320,805 | 6/1994 | Kramer et al. | 422/37 X |

FOREIGN PATENT DOCUMENTS

| | | |
|---|---|---|
| 1099293 | 1/1968 | United Kingdom . |
| WO92/19287 | 11/1992 | WIPO . |

OTHER PUBLICATIONS

Chemical Abstracts, vol. 98, No. 7, Feb. 14, 1983, Abstract No. 52223t, "Preservative-coated Food Packaging Materials," p. 538, JP, A2 57153873, (Kokai Tokkyo Koho), 22 Sep. 1982.

Primary Examiner—Robert J. Warden
Assistant Examiner—Krisanne M. Thornton
Attorney, Agent, or Firm—Burns, Doane, Swecker & Mathis, L.L.P.

[57] ABSTRACT

A process is provided for the sterilization of the surface of a packaging material, e.g. a plastic coated board, by contacting such material with a hydrogen peroxide solution, wherein the hydrogen peroxide solution is modified by the addition thereto of a penetration-reducing amount of a penetration-reducing salt. The salt referred to is preferably an alkali metal salt, for instance, a sulphate or halogenide, such as sodium sulphate or sodium chloride. A composition is provided that is useful for carrying the sterilization process into effect, wherein a hydrogen peroxide solution is modified by the addition of a penetration-reducing amount of a penetration-reducing salt.

23 Claims, No Drawings

STERILIZATION PROCESS

TECHNICAL FIELD OF THE INVENTION

The present invention relates to the field of sterilization of packaging materials in connection with the use of said materials for the packaging of substances which must not be contaminated with microorganisms, for instance food stuffs and beverages, More specifically the invention is within the field of sterilization of such materials by means of hydrogen peroxide as the sterilization agent.

BACKGROUND OF THE INVENTION

For certain packaging material grades, especially such materials which are intended to be used for food stuffs, beverages, etc., a sterilization of the surface thereof is required in order to minimize the contribution of microorganisms from the packaging material to the product duct to be contained therein. One of said sterilization methods involves the use of hydrogen peroxide as the sterilization agent, There are different methods of applying said hydrogen peroxide to the packaging material, such as by passing the packaging material through the hydrogen peroxide, immersing said material in said hydrogen peroxide, applying a film of hydrogen peroxide to the surface of the packaging material, etc., but generally the hydrogen peroxide is utilized in the form of a solution thereof, especially an aqueous solution.

Although the packaging material has generally been made hydrofobic during the manufacture thereof, in order to make it resistant to the penetration of aqueous liquids including a hydrogen peroxide solution, the hydrogen peroxide is usually utilized in such a concentration and at such a temperature that a penetration thereof into the packaging material is not easily avoided. The hot aquecus hydrogen peroxide solution especially penetrates the edges of the packaging material, but also in a case where for some reason the packaging machine has to be stopped, there will be a great risk of having a penetration of the hot hydrogen peroxide into the packaging material to loosen up the same. When restarting the machine part of the packaging material has to be discarded or else there will be a risk of having a bursting of any package inside the machine which means a cleaning operation for several hours.

Thus, in summary, there is no available system today which will impart to the packaging material such a degree of hydrofobicity that a penetration of a concentrated and hot hydrogen peroxide solution is avoided.

OBJECT OF THE INVENTION

The main object of the present invention is to modify the previously known sterilization process where a solution of hydrogen peroxide is utilized to manufacture an aseptic packaging material so as to greatly reduce the penetration, especially the edge penetration, of the hydrogen peroxide solution into the packaging material. Other objects of the invention will be apperent to a person skilled in the art when reading the description of the present invention.

GENERAL DESCRIPTION OF THE INVENTION

According to the present invention it has been shown that the above-mentioned object can be achieved by the addition of a salt to the hydrogen peroxide solution, which salt counteracts the penetration of the hydrogen peroxide into the packaging material. Thus, in accordance with the present invention it has been found that said penetration may be decreased or reduced with at least 50%, which means a very significant improvement within the art of manufacturing aseptic packages, as said manufacturing takes place at very high rates and quantities.

More specifically the invention relates to a process for the sterilization of the surface of a packaging material by contacting said material with a hydrogen peroxide solution, characterized by modifying the hydrogen peroxide solution by the addition thereto of a penetration-reducing amount of a penetration-reducing salt.

The invention also relates to a composition which is useful for the sterilization of the surfaces of a packaging material of the type referred to, which comprises a hydrogen peroxide solution, characterized in that it comprises a penetration-reducing amount of a penetration-reducing salt.

DETAILED DESCRIPTION OF THE INVENTION

Generally the process according to the invention is applicable to the sterilization of any packaging material for which hydrogen peroxide solutions have been previously utilized. Especially interesting packaging materials in connection with the invention are, however, paper board and more specifically a hydrophobated board. With reference to hydrophobated board this generally means that the board has been coated with a hydrophobic film such as plastic or wax according to any known technique. Such packaging materials are for instance utilized in the packaging of different beverages, e.g. long life milk.

Now that the inventive idea has been disclosed it should be possible to a person skilled in the art to determine whether any salt will be useful for the practice of the invention or not. Generally, however, the requirement as to the penetration-reducing salt is that it is reasonably soluble in the hydrogen peroxide solution and that it does not catalyze the decomposition of the hydrogen peroxide to any substantial extent, i.e. not to such an extent that the sterilization effect is adversely influenced upon. Expressed in another way a suitable penetration-reducing salt for use in accordance with the invention includes any salt which reduces the penetration of a hydrogen peroxide sterilization solution into a hydro-phobated board and which is compatible with the hydrogen peroxide solution is useful in accordance with the invention. Compatible in this sence may e.g. mean that the hydrogen peroxide concentration is not reduced to any substantial extent, for instance not more than 10%, or not more than 5%, during 1 week or even 2 weeks.

According to the invention it has been found that for instance alkali metal salt are preferable as to the non-penetration of the hydrogen peroxide. An especially preferable embodiment of the process of the invention means that a sodium salt is utilized.

Other potential salts for use in accordance with the invention may be selected from the group of alkaline earth metals, especially calcium and magnesium. Furthermore, aluminum salts should be useful in accordance with the invention.

According to another preferable embodiment of the invention the hydrogen peroxide solution is modified with a salt selected from the group consisting of sulphates and halogenides, preferably chlorides.

From the above-mentioned it can also be gathered that specifically interesting salts for the modification of the hydrogen peroxide solution are sodium sulphate and sodium chloride.

The salt referred to is generally used in a penetration-reducing amount, which should be easily determinable by a person skilled in the art, especially by means of the Wick index method which will be described more in detail below. However, a penetration-reducing amount of said salt is a concentration which reduces the Wick index of the paper board preferably by at least 20%, more preferably by at least 30% and most preferably by at least 40%. Generally, the solubility of the salt in hydrogen peroxide dictates the upper limit of the concentration range. However, in order to minimize the depositions of salts in the packaging machine a concentration as low as possible is aimed at. A preferable salt concentration may also be defined as 0.5–1 mole/liter. Toxicity considerations should of course also be taken in the usual way when food stuffs and beverages are involved.

With reference to the contact between the packaging material and the hydrogen peroxide solution said contact is generally performed in accordance with the prior art, which preferably means that a hot aqueous hydrogen peroxide solution is used. The term hot is used in a broad meaning in accordance with the known technique, but according to a preferable embodiment of the process of the invention the temperature of the hydrogen peroxide solution is within the range of 50°–80 C., especially good results being achieved at a temperature of the order of 700° C.

The concentration of the hydrogen peroxide solution, i.e. as to the contents thereof of $H_2O_2$, is generally similar to that used according to the prior art, However, a preferable embodiment of the present invention involves the use of a solution that is 10–40% as to its hydrogen peroxide content, the percentage being calculated in accordance with current practice within this field. Especially preferable results are generally achieved with a hydrogen peroxide solution having a concentration of the order of 35%.

Also with reference to the pH-value of the hydrogen peroxide solution the general principles of the current art are applicable. Thus, also with the addition of the salt in accordance with the invention, which salt may well influence upon the pH of the solution, the previously known pH ranges are useful. Especially preferable results as to non-penetration in accordance with the invention are, however, obtained at a pH-value of the modified hydrogen peroxide solution within the range of 1–4, the range of 1.5–2.5 being especially preferable.

The contact between the packaging material and the modified hydrogen peroxide solution can take place in accordance with any one of the known techniques. Thus, in this respect, reference is made to the prior art as concerns details of the different techniques utilized. According the preferable embodiment of the process claimed the packaging material is, however, contacted with the hydrogen peroxide solution by passing the material therethrough in a continuous way.

Preferable embodiments of the composition according to the invention are the same as have been described in connection with the process claimed and will not be repeated here.

The process as well as the composition according to the invention will now be more specifically illustrated by means of the following non-limiting examples.

EXAMPLES 142 g of sodium sulphate were added to one liter of hydrogen peroxide. The concentration of the hydrogen peroxide was adjusted to 35%.

A plastic coated board was prepared and immersed into hot (70° C.) hydrogen peroxide solution for 10 minutes and the amount of liquid which had penetrated into the board was determined in accordance with the edge wicking method that will be described below and expressed as the Wick index. The Wick index was found to be 0.5 $kg/m^2$ which should be compared to a corresponding Wick index value of 0.9 $kg/m^2$ for a control (i.e. without any addition of salt).

The above experiment was repeated with sodium chloride in different concentrations. The addition of the salt means that the concentration or percentage of the hydrogen peroxide is reduced, and in addition thereto it was found that the pH decreased. Therefore, if the specifications for the Wick test are to be followed one has to start from a hydrogen peroxide having a higher concentration than the one desired and optionally adjust the concentration and pH after the addition of the salt. The solutions tested are presented in Table 1. Furthermore, $NaHCO_3$ was also tested but a slow evolution of gas was noted which indicates that it catalyzes the decomposition of the hydrogen peroxide. Thus, the test with $NaHCO_3$ discontinued.

TABLE 1

| Test | Weight % | pH |
| --- | --- | --- |
| 35% $H_2O_2$ | 36.0 | 2.30 |
| +1.0M NaCl | 34.1 | 1.64 |
| +2.0M NaCl | 32.4 | 1.60 |
| +3.0M NaCl | 30.7 | 1.49 |

With the above-mentioned solutions the edge penetration measurements were made, and in Table 2 the results thereof are presented.

TABLE 2

| Test | Wick (I) ($kg/m^2$) | Wick (II) ($kg/m^2$) |
| --- | --- | --- |
| 35% $H_2O_2$ | 1.15 | 0.96 |
| +1.0M NaCl | 0.79 | 0.66 |
| +2.0M NaCl | 0.65 | 0.52 |
| +3.0M Nacl | 0.55 | 0.45 |

In this case Wick (I) means that the pH-value was not adjusted after the salt addition while Wick (II) refers to such a pH adjustment. As is clear from this table the adjustment of the pH was of marginal influence only.

In order to investigate the effects of the dilutions obtained by the salt additions some experiments were made where the 36% hydrogen peroxide was diluted to 34% and respectively. The results thereof are presented in Table 3.

TABLE 3

| Conc. (%) | Wick ($kg/m^2$) |
| --- | --- |
| 36 | 0.91 |
| 34 | 0.88 |
| 30 | 0.81 |

As can be seen the effect of a lower hydrogen peroxide concentration is a lower Wick value. The value obtained for 30% hydrogen peroxide should be compared to the value obtained with 3 M NaCl (0 45–0.55 g).

Then the effects of NaCl with a proper hydrogen peroxide concentration (35%) and with adjusted pH values were investigated. The results thereof are presented in Table 4.

TABLE 4

| Test | Wick (kg/m$^2$) |
| --- | --- |
| Blank 35% | 0.92 |
| +2M NaCl | 0.61 |
| +3M NaCl | 0.57 |

As is clear from the above Table the results for added salts are significantly superior also when the hydrogen peroxide concentration is the proper one according to the test method.

The first result presented above with reference to sodium sulphate was supplemented with additional results as to sodium sulphate in accordance with Table 5 below.

TABLE 5

| Test | Conc. (%) | Wick (kg/m$^2$) | pH |
| --- | --- | --- | --- |
| Blank | 35 | 0.91 | 2.4 |
| 1M Na$_2$SO$_4$ | 31.8 | 0.57 | 2.8 direct |
| 1M Na$_2$SO$_4$ | 31.8 | 0.49 | 2.4 adjusted pH |
| 1M Na$_2$SO$_4$ | 35.0 | 0.49 | 2.4 |

As can be seen from the above-mentioned Table, contrary to what was obtained by the addition of sodium chloride, the pH value increased by the addition of the sulphate. Furthermore, it can be seen that the effect on the Wick value is higher with the sodium sulphate. Thus, with 1 M Na$_2$SO$_4$ the result is similar to that obtained with 3 M NaCl.

Different other salts were also tested in a way similar to that described above. The results thereof as to decomposition of hydrogen peroxide are presented in Table 6, the concentration being chosen so as to obtain an ionic strength of 3.0.

TABLE 6

| Salt | Conc. (M) | Conc. directly (% by weight of H$_2$O$_2$) | Conc. 1 week (% by weight of H$_2$O$_2$) | Conc. 2 weeks (% by weight of H$_2$O$_2$) |
| --- | --- | --- | --- | --- |
| Na$_4$P$_2$O$_7$ | 0.3 | 47.0 | — | 43.6 |
| Na Acetate | 3.0 | 33.8 | — | 31.1 |
| CaCl$_2$ | 1.0 | 44.4 | — | 42.2 |
| Alum* | 0.2 | 44.4 | — | 0.5 |
| Na$_2$SO$_4$ | 0.5 | 34.9 | 34.9 | — |
| Na$_2$SO$_4$ | 1.0 | 44.7 | 44.5 | — |
| Na$_2$SO$_4$ | 2.0 | 39.9 | 39.8 | — |

*Al$_2$(SO$_4$)$_3$

Also Na$_3$PO$_4$ was tested but said test was discontinued due to gas evolution indicating the decompostion of the hydrogen peroxide.

As is clear from Table 6 the decomposition of the hydrogen peroxide varies to a great extent with the different salts used. The bad result obtained with alum is probably due to the presence of iron therein.

The effects of the salts above, except for alum were tested at 70° C. with the hydrogen peroxide concentration adjusted to 35%. As is seen in Table 6 above the hydrogen peroxide concentration falls below 35% if 3.0 M Na acetate is used.

As 50% hydrogen peroxide was initially used, it was not possible to use more than 2.76 moles per liter of sodium acetate.

The results are presented in Table 7.

TABLE 7

| Salt | Conc. (M) | Wick (g/m$^2$) |
| --- | --- | --- |
| Na$_4$P$_2$O$_7$ | 0.3 | 1.6 |
| Na Acetate | 2.76 | 1.8 |
| CaCl$_2$ | 1.0 | 0.86 |
| Na$_2$SO$_4$ | 0.5 | 0.85 |
| Na$_2$SO$_4$ | 1.0 | 0.55 |
| Na$_2$SO$_4$ | 2.0 | 0.54 |
| Blank | — | 1.5 |

One test was also made at 60° C., viz. with 1 M of Na$_2$SO$_4$. The result was comparable to that obtained at 70° C. (Table 6 above).

Finally, with reference to the Wick values referred to above, the following test method was used.

EDGE WICKING OF SIZED PAPER AND PAPER BOARD (70° C., 10 min 35% hydrogen peroxide)

DEFINITION

The edge wicking test is a method to determine how well a paper is sized against the specified test solution.

The edge wicking index (EWI) in this test is defined as the amount of liquid absorbed by the edges of test pieces placed for 10 minutes in hydrogen peroxide (H$_2$O$_2$).

The result is given in kg/m$^2$ and the testing conditions (time and temperature) must be reported.

EQUIPMENT water bath with thermostat
analytical balance (with readability of 0.1 mg)
guillotine
stop watch
tape, water resistant e.g. Scotch El-tape No. 5 from 3 M Co
dish, e.g. crystallizing dish of Duran glass
rods of glass or stainless steel
measuring glass
beaker
blotting paper
thermometer (with readability of 1° C.)

TEST SOLUTION

Hydrogen peroxide (Food grade) 35% by weight. Density 1130 kg/m$^3$. pH 1.5 to 2.5. (same quality as used in AB8 and AB9).

TEST PROCEDURE

1. Preparation of test pieces

The raw paper should be conditioned according to TP 85013 (modified SCAN P2: 75).

TP 85013 specifies:

Proconditioning a= 60° C. for 30 minutes and the conditioning at 23° C.±1° C. and 50% RH±2% RH for at least 3 hours.

For raw paper cover the printing and the back sides of the test material carefully with water resistant tape. Make sure there are no air bubbles between the paper and the tape.

For laminated material tape is not necessary. Cut out 10 test pieces. Two (2) series with five (5) test samples in each. The test pieces should be 25 mm (MD)×75 mm (CD).

Please note that the cutting edges of the guillotine must be sharp in order to get well cut edges. The edges must be pressed against each other and the test piece removed before the cutting edges are separated, otherwise the fibre structure of the edges can be disturbed.

2. Thickness measurement

Measure the thickness of the sample. For laminated material, the thickness for polyethylene and aluminum foil should be subtracted.

Only the paper thickness is needed.

A mean value of the thickness for five test pieces should be used in the calculations.

3. Edge wicking test

Weigh each series of five (5) test pieces together up to the nearest mg on an analytical balance. At least two (2) series are preferable.

Pour hydrogen peroxide in a flat bottomed glass dish. Place the glass dish in a water bath and wait until the hydrogen peroxide has reached 70° C.±1° C.

Place the test pieces in the glass dish so they do not touch each other and put glass rods on top.

Make sure that the test pieces are covered by 10 mm± 1 mm of hydrogen peroxide.

Remove the test pieces after 10 minutes± 15 seconds and place them between two blotting papers and wipe off excessive liquid. Avoid hard pressing on the surface and avoid touching the edges.

During these operations wear gloves and safety glasses (see Appendix 1).

The water bath with the peroxide should preferably be placed in a closed hood or under a well ventilated hood.

Weigh at once each series of five (5) test pieces together up to the nearest mg.

Note:

Hydrogen peroxide may evaporate during tests. Hence, it is necessary to add more hydrogen peroxide so the test pieces always are covered with 10 mm± 1 mm of liquid.

Start every day's measurements with fresh solution of hydrogen peroxide.

CALCULATION $W_1$= weight before (mg) contact with hydrogen peroxide
$W_2$= weight after (mg) contact with hydrogen peroxide
t=thickness (μm), a mean value for five (5) test pieces
$\lambda$= sample edge length (m) 1 m $$\text{Edge wicking index} = \frac{W_2 - W_1}{\lambda \times t}$$

For each series of five (5) test pieces:

$\lambda$= 1, i.e. 5×(75 mm+ 75 mm+ 25 mm+ 25 mm)=1000 mm=1 m $$\text{Edge wicking index}(EWI) = \frac{W_2 - W_1(\text{mg})}{t(\mu m) \times 1 \text{ m}}$$

which gives a value in the unit kg/m²

Remark 1

If the thickness of the base board is unknown the edge wicking value (EWV) should be reported as mg/m.

Hence, for each series of five (5) test pieces $\lambda$= 1, i.e. 5×(75 mm+ 75 mm+ 25 mm+ 25 mm)=1000 mm=1 m $$\text{Edge wicking value}(EWV) = \frac{W_2 - W_1(\text{mg})}{1 \text{ m}} \ [\text{mg/m}]$$

RESULT

The edge wicking index will be reported in kg/m². Temperature and time must be specified.

If two or more series are carried out, a mean value should be reported.

We claim:

1. A process for the sterilization of the surfaces of a packaging material comprising providing a packaging material and contacting said material with a hydrogen peroxide solution that is modified by the inclusion of a penetration-reducing amount of a penetration-reducing salt.

2. A process according to claim 1 wherein the hydrogen peroxide solution is modified with an alkali metal salt.

3. A process according to claim 1, wherein the hydrogen peroxide solution is modified with an alkaline earth metal salt.

4. A process according to claim 1, wherein the hydrogen peroxide solution is modified with a salt selected from the group consisting of sulphates and halogenides.

5. A process according to claim 1, wherein the hydrogen peroxide solution is modified with $Na_2SO_4$ or NaCl.

6. A process according to claim 1 wherein the hydrogen peroxide solution is modified with said salt in an amount which reduces the edge wicking index by at least 20% relative to the edge wicking index obtained without the addition of said salt.

7. A process according to claim 1 wherein said packaging material is contacted with a modified hot aqueous hydrogen peroxide solution at a temperature within the range of 50°–80° C.

8. A process according to claim 1 wherein said packaging material is contacted with a modified 10–40% hydrogen peroxide solution.

9. A process according to claim 1 wherein said packaging material is contacted with a modified hydrogen peroxide solution, the pH of which is within the range of 1–4.

10. A process according to claim 1 wherein said packaging material is contacted with the hydrogen peroxide solution by passing the packaging material therethrough.

11. A process according to claim 2 wherein the hydrogen peroxide solution is modified with a salt selected from the group consisting of sulphates and halogenides.

12. A process according to claim 3 wherein the hydrogen peroxide solution is modified with a salt selected from the group consisting of sulphates and halogenides.

13. A process according to claim 1 wherein said packaging material possesses a hydrophobic surface.

14. A process according to claim 1 wherein said packaging material possesses a hydrophobic plastic coating upon the surface thereof.

15. A process according to claim 2 wherein said alkali metal salt is a sodium salt.

16. A process according to claim 3 wherein said alkaline earth metal salt is a calcium or magnesium salt.

17. A process according to claim 4 wherein said salt is a chloride.

18. A process according to claim 5 wherein said edge wicking index is reduced by at least 30%.

19. A process according to claim 5 wherein said edge wicking index is reduced by at least 40%.

20. A process according to claim 7 wherein the temperature is approximately 70° C.

21. A process according to claim 8 wherein said modified hydrogen peroxide solution contains approximately 35% hydrogen peroxide.

22. A process according to claim 9 wherein said modified hydrogen peroxide solution has a pH within the range of 1.5–2.5.

23. A process according to claim 10 wherein said packaging material is continuously passed through said hydrogen peroxide solution.

* * * * *